(12) United States Patent
Plaskos et al.

(10) Patent No.: US 8,096,997 B2
(45) Date of Patent: Jan. 17, 2012

(54) GUIDING DEVICE FOR BONE CUTTING

(75) Inventors: Christopher Plaskos, New York, NY (US); Stephane Lavallee, Saint Martin d'Uriage (FR); Guillaume Champleboux, Voiron (FR)

(73) Assignee: Perception Raisonnement Action en Medecine, La Tronche (FR)

( * ) Notice: Subject to any disclaimer, the term of this patent is extended or adjusted under 35 U.S.C. 154(b) by 1462 days.

(21) Appl. No.: 11/305,887

(22) Filed: Dec. 16, 2005

(65) Prior Publication Data
US 2006/0200161 A1 Sep. 7, 2006

Related U.S. Application Data

(63) Continuation of application No. PCT/FR2004/050227, filed on Jun. 18, 2004.

(30) Foreign Application Priority Data

Jun. 18, 2003 (FR) ...................................... 03 07346

(51) Int. Cl.
*A61B 17/58* (2006.01)
(52) U.S. Cl. ........................................................ 606/88
(58) Field of Classification Search .................... 606/86, 606/87, 88, 89, 86 R, 96–98
See application file for complete search history.

(56) References Cited

U.S. PATENT DOCUMENTS

| | | | |
|---|---|---|---|
| 4,457,307 A * | 7/1984 | Stillwell | 606/88 |
| 5,417,695 A * | 5/1995 | Axelson, Jr. | 606/89 |
| 5,454,816 A * | 10/1995 | Ashby | 606/88 |
| 5,474,559 A * | 12/1995 | Bertin et al. | 606/89 |
| 5,601,563 A * | 2/1997 | Burke et al. | 606/86 R |
| 5,653,714 A | 8/1997 | Dietz et al. | |
| 5,683,397 A * | 11/1997 | Vendrely et al. | 606/88 |
| 5,769,855 A * | 6/1998 | Bertin et al. | 606/88 |
| 5,860,981 A | 1/1999 | Bertin et al. | |
| 6,056,754 A * | 5/2000 | Haines et al. | 606/80 |
| 6,554,837 B1 * | 4/2003 | Hauri et al. | 606/87 |
| 6,558,391 B2 * | 5/2003 | Axelson et al. | 606/88 |
| 6,575,980 B1 * | 6/2003 | Robie et al. | 606/88 |
| 6,702,821 B2 * | 3/2004 | Bonutti | 606/88 |
| 6,712,824 B2 * | 3/2004 | Millard et al. | 606/87 |
| 7,029,477 B2 * | 4/2006 | Grimm | 606/88 |
| 7,488,324 B1 * | 2/2009 | Metzger et al. | 606/89 |
| 7,520,880 B2 * | 4/2009 | Claypool et al. | 606/88 |
| 7,547,307 B2 * | 6/2009 | Carson et al. | 606/88 |
| 7,569,060 B2 * | 8/2009 | Faoro | 606/87 |
| 2004/0039396 A1 * | 2/2004 | Couture et al. | 606/87 |
| 2006/0015114 A1 * | 1/2006 | Bernardoni et al. | 606/87 |

FOREIGN PATENT DOCUMENTS

WO WO-98/32384 7/1998

* cited by examiner

*Primary Examiner* — Thomas C. Barrett
*Assistant Examiner* — Christopher Beccia
(74) *Attorney, Agent, or Firm* — Panitch Schwarze Belisario & Nadel LLP

(57) ABSTRACT

A device for guiding a cutting tool capable of cutting bone portions at the level of the head of a bone includes a seat intended to be fastened at the level of said head defining a first rotation axis (Γ). The device includes means for adjusting the position of the first rotation axis with respect to said seat and an arm, with one end of said arm being pivotally assembled on said seat according to the first rotation axis. A guide intended to support the tool is pivotally assembled on the arm according to a second rotation axis (Δ).

26 Claims, 4 Drawing Sheets

GUIDING DEVICE FOR BONE CUTTING

CROSS-REFERENCE TO RELATED APPLICATION

The present application is a continuation of PCT International Application Serial No. PCT/FR2004/050227, filed Jun. 18, 2004, claiming priority of French Application No. 03/07346, filed Jun. 18, 2003. The PCI International Application published as WO 2004/112620 on Dec. 29, 2004 in the French language. Both applications are hereby incorporated by reference in their entirety.

TECHNICAL FIELD

The present invention relates to a device for guiding a bone cutting.

BACKGROUND

Some surgical operations, for example, hip or knee arthroplasty, require at least one bone cut at the level of the head of a long bone to arrange a prosthesis. Bone cutting is performed by means of a cutting tool, for example, a miller or an oscillating saw, maintained in position by a cutting guide attached to the bone. Generally, several bone cut must be successively performed in distinct planes at the level of a same bone head. It is then necessary to accurately determine the relative positions between the cutting planes, while ensuring a surface state of sufficient quality for each cutting plane.

U.S. Pat. No. 4,457,307 describes a device for guiding a cutting tool to perform successive cuttings to arrange a knee prosthesis. The device comprises a seat intended to be fastened on the femur diaphysis. A cutting guide is pivotally assembled on arms, themselves pivotally assembled on the seat. The guide can then be displaced with respect to the seat to define the cutting planes. A saw is maintained by the guide as the bone cuttings are performed. A disadvantage of such a device is that it is relatively bulky.

U.S. Pat. No. 5,653,714 describes a device for guiding a bone cutting tool to perform successive bone cuttings along distinct cutting planes exhibiting a reduced bulk.

The present invention aims at obtaining an alternative cutting guide adapted to the performing of a bone cutting, or of several successive bone cuttings along different cutting planes, exhibiting a reduced bulk.

The present invention also aims at obtaining a cutting guide of particularly simple structure and kinematics.

To achieve these objects, the present invention provides a device for guiding a cutting tool capable of cutting bone portions at the level of the head of a bone, comprising a seat intended to be fastened at the level of said head defining a first rotation axis; means for adjusting the position of the first rotation axis with respect to said seat; an arm, one end of said arm being pivotally assembled on said seat according to the first rotation axis; and a guide intended to support the tool and pivotally assembled on the arm according to a second rotation axis (Δ).

According to an embodiment of the present invention, the guiding device comprises two seats intended to be fastened at the level of said head in substantially opposite fashion with respect to said head and defining a first rotation axis; means for adjusting the position of the first rotation axis with respect to the seats; two arms, one end of each arm being pivotally assembled on a seat according to the first rotation axis; and a guide extending substantially transversally to said head, and pivotally assembled at two ends on the arms according to a second rotation axis, the maximum swinging angle of the guide around the first rotation axis being greater than 100 degrees.

According to an embodiment of the present invention, one of the arms is connected to a seat by a pin joint, the adjustment system being arranged between said seat and said pin joint and being capable of modifying the position of said pin joint with respect to said seat according to two directions substantially tangent to said head.

According to an embodiment of the present invention, the device comprises a first actuating gear capable of rotating at least one arm around the first rotation axis and a second actuating gear capable of rotating the guide around the second rotation axis.

According to an embodiment of the present invention, the device comprises a connection element connecting the two seats by at least partially surrounding said head.

According to an embodiment of the present invention, the adjustment means are arranged between one of the seats and the connection element.

According to an embodiment of the present invention, the device comprises means for displacing one of the seats with respect to the connection element in a direction transversal to said head.

According to an embodiment of the present invention, each seat comprises at least one pick intended to come in contact with said head.

According to an embodiment of the present invention, the guide comprises at least one opening for guiding the cutting tool.

According to an embodiment of the present invention, the cutting tool is a mill.

According to an embodiment of the present invention, the cutting tool is an oscillating saw.

BRIEF DESCRIPTION OF THE DRAWING FIGURES

The foregoing objects, features, and advantages, as well as others of the present invention will be discussed in detail in the following non-limiting description of specific embodiments in connection with the accompanying drawings, among which:

Figure 1:
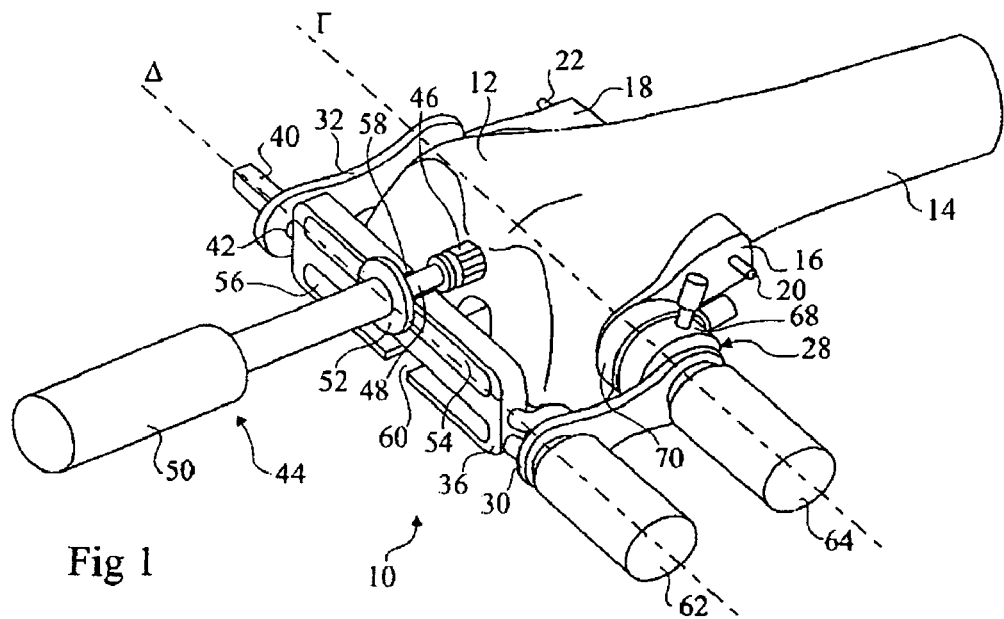
FIG. 1 shows a perspective view of a first example of embodiment of the cutting guide according to the present invention.
Figure 3:
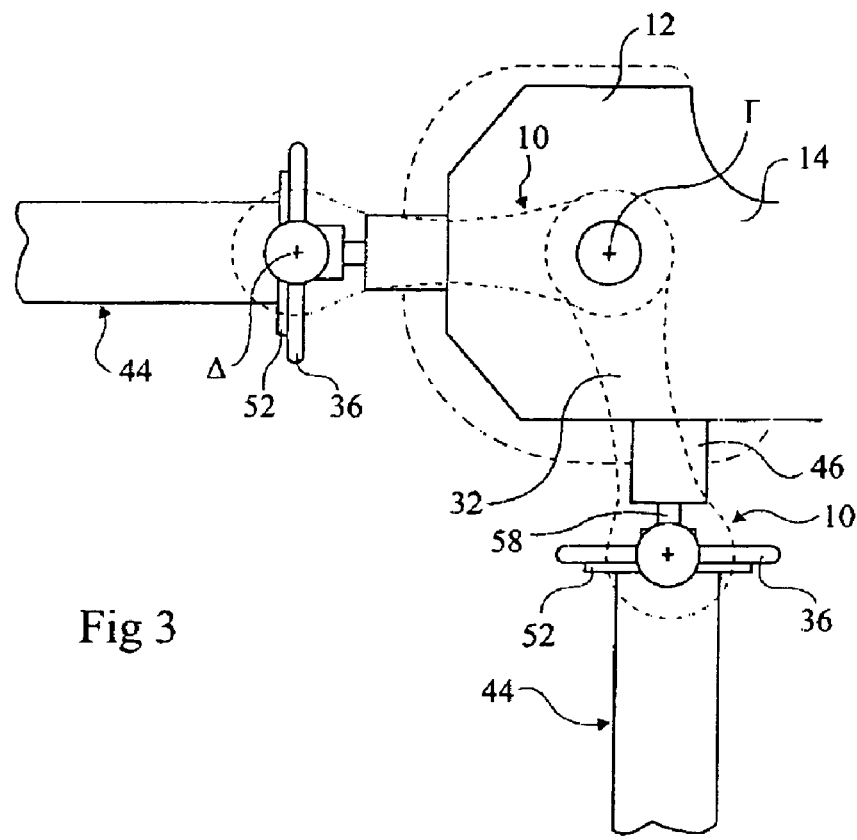
Figure 4:
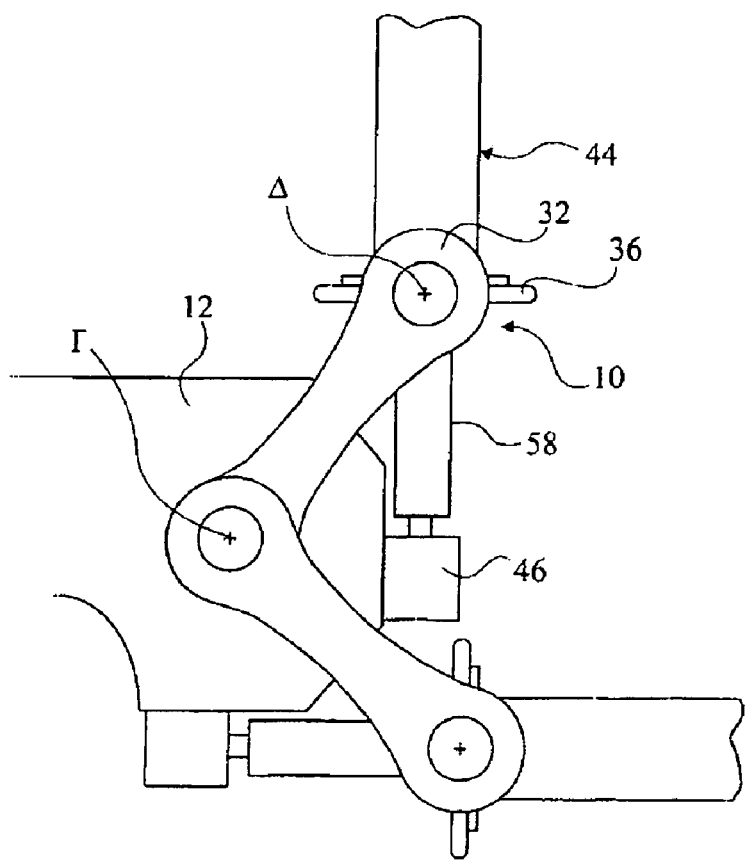
Figure 5:
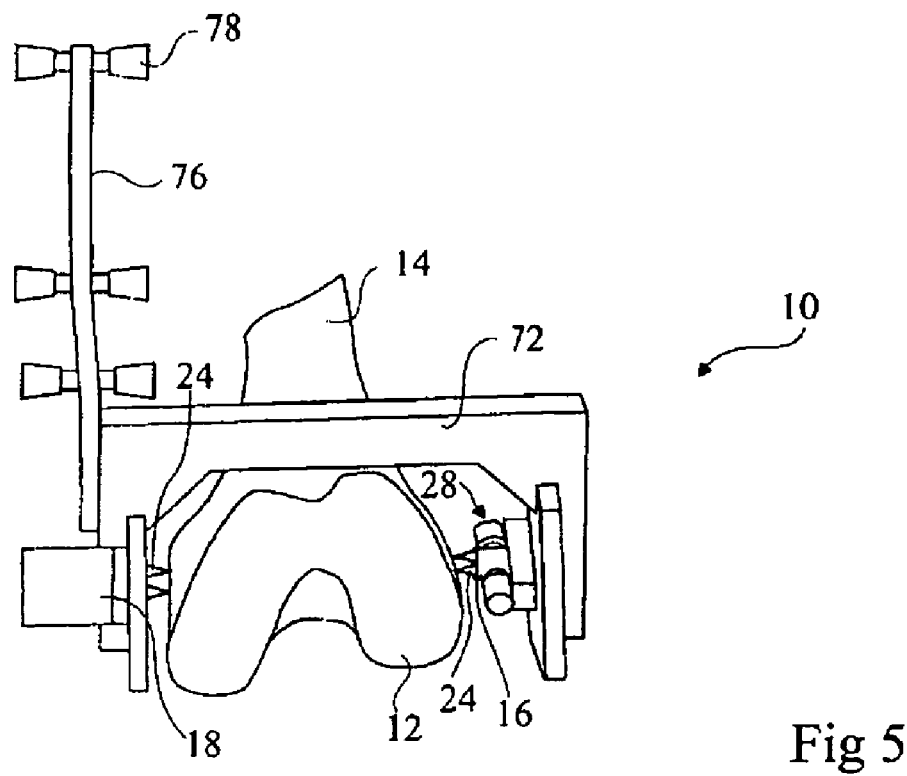
Figure 6:
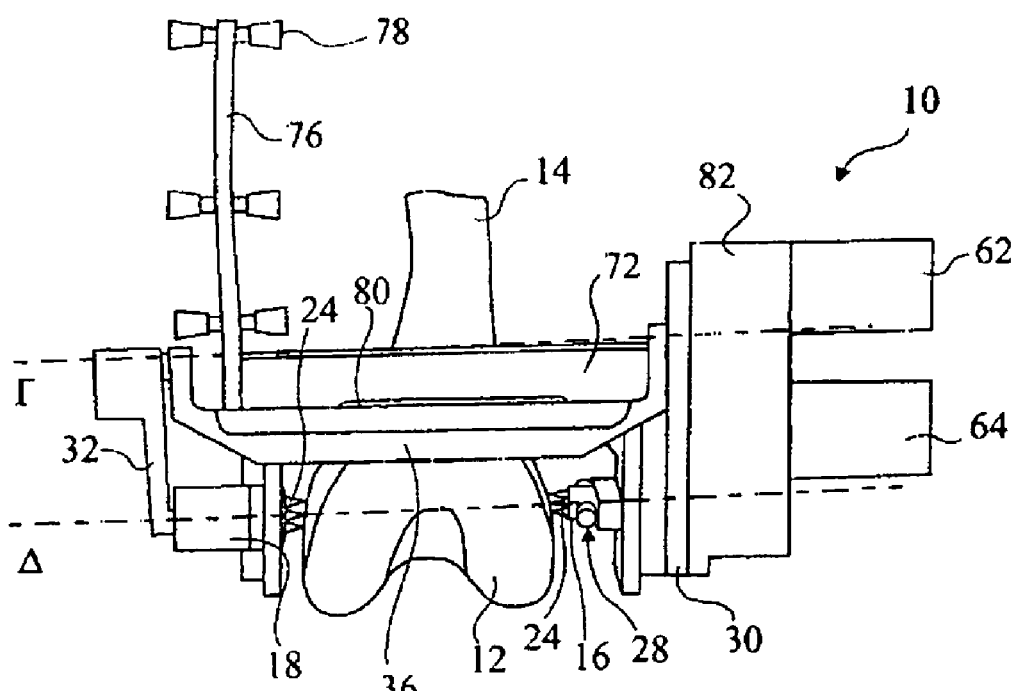
Figure 7:
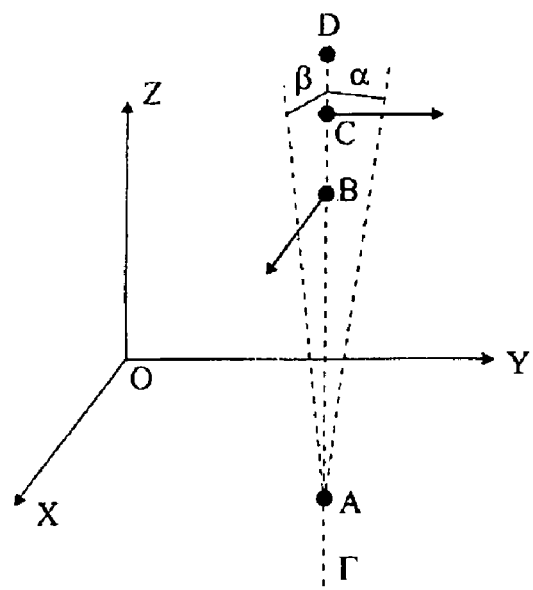
Figure 8:
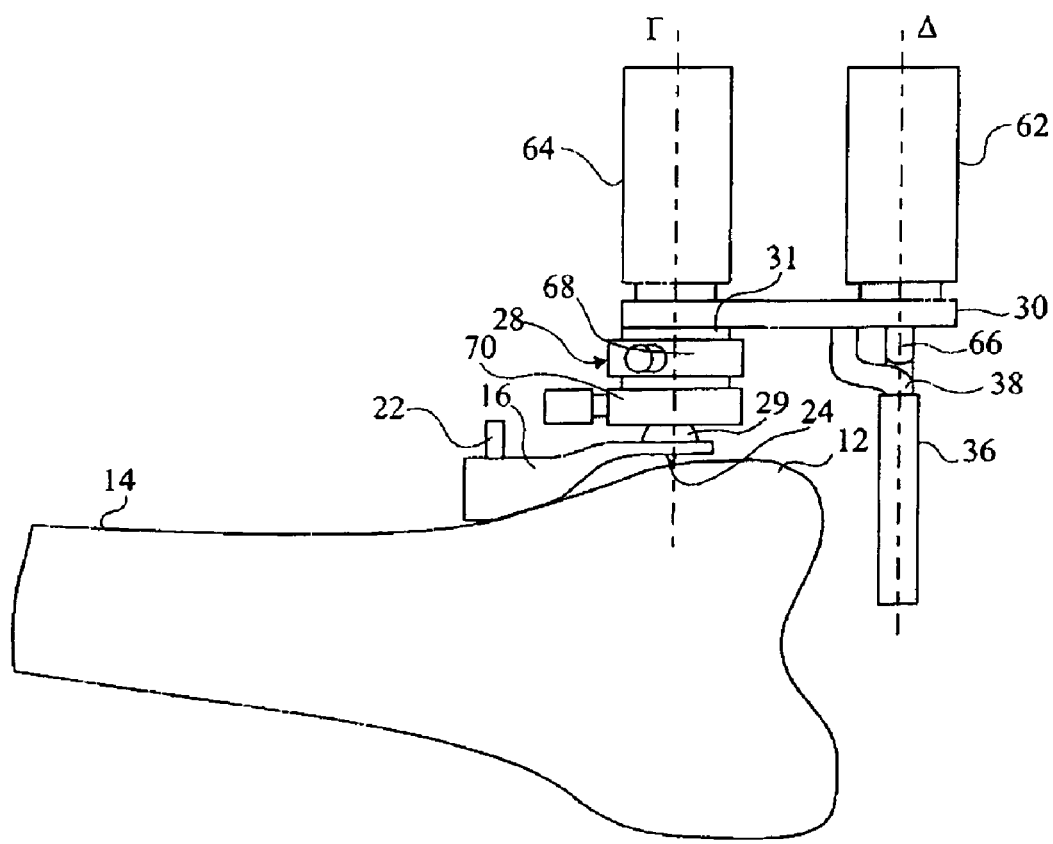

FIG. 3 schematically shows side views of the device of FIG. 1 in the forming of several cutting planes;

FIG. 4 shows views similar to FIG. 3 for an alternative use of the device of FIG. 1;

FIG. 5 shows a perspective view of elements of a second example of embodiment of the guiding device according to the present invention;

FIG. 6 shows a perspective view of the entire device of FIG. 5;

FIG. 7 schematically illustrates the principle of the position setting of the device according to the present invention; and FIG. 8 shows a top view of a third example of embodiment of the cutting guide according to the present invention.

DETAILED DESCRIPTION OF THE PREFERRED EMBODIMENTS

Figure 2:
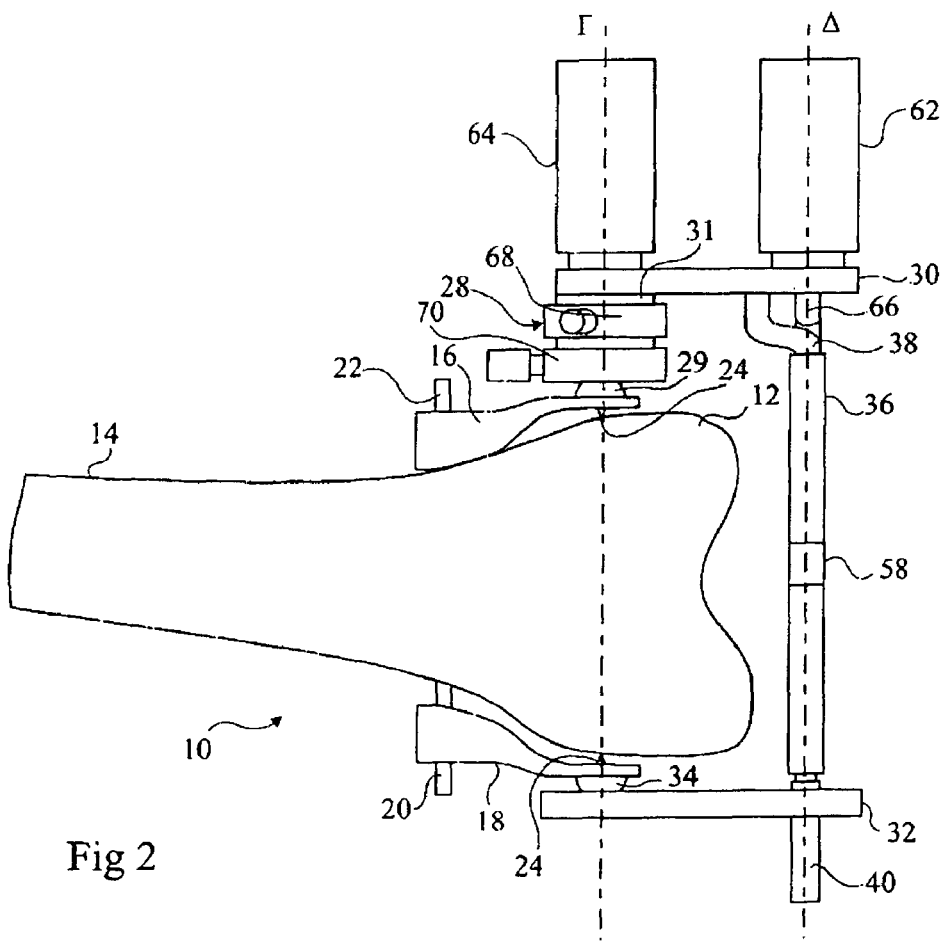
FIG. 2 shows a top view of the device of FIG. 1.

As shown in FIGS. 1 and 2, cutting guide 10 according to the present invention is arranged at the level of head 12 of a long bone 14. It for example is the femur, the tibia, the humerus, etc. Device 10 comprises two seats 16, 18 fastened to head 12 of bone 14 via pins 20, 22. Each seat 16, 18 comprises a pick 24 for arranging seat 16, 18 on head 12 before definitive fastening of seat 16, 18 by means of the associated pin 20, 22.

An adjustment system 28 is assembled on seat 16 via a ball and socket joint 29. An arm 30 is pivotally assembled on adjustment system 28 via a pin joint 31. An arm 32 is movably assembled on seat 18 via a ball and socket joint 34.

Device 10 comprises a cutting guide 36 which extends between arms 30, 36. One end of cutting guide 36 is pivotally assembled on a lever 38 attached to arm 30 according a rotation axis Δ. The opposite end 40 of cutting guide 36 is pivotally mounted in an opening 42 of arm 32. The connection between arms 30, 32 imposed by cutting guide 36 substantially limits the motion of arms 30, 32 with respect to seats 16, 18 to a rotation motion around a rotation axis Γ.

Cutting guide 36 is intended to receive a cutting tool 44, only shown in FIG. 1. In the present example of embodiment, cutting tool 44 is a miller comprising a mill 46 arranged at the end of a shaft 48 driven by an electric motor 50. Cutting tool 44 also comprises a bearing sure 52 intended to stop against guide 36 and which extends in a plane substantially perpendicular to the axis of shaft 48. Bearing surface 52 maintains shaft 48 in a direction substantially perpendicular to axis Δ when an operator applies tool 44 against guide 36. Guide 36 is crossed by two substantially straight parallel grooves 54, 56 which extend along axis Δ in which driving shaft 48 can slide. Two notches 58, 60 are provided to enable insertion of driving shaft 48 into one of grooves 54, 56. Cutting tool 44 comprises means (not shown) for setting the distance separating mill 46 from bearing surface 52.

Two electric motors 62, 64 are supported by arm 30. The supply and control means of motors 62, 64 are not shown. Electric motor 62 is capable of rotating guide 36 around axis (Δ). For this purpose, the driving shaft of electric motor 62 is connected to guide 36 via a bent arm 66. Electric motor 64 is intended to rotate arm 30 around rotation axis F. Motors 62, 64 may be controlled by a computer, not shown.

Adjustment system 28 enables accurately setting the position of pin joint 31 with respect to seat 16 to allow, on assembly of guiding device 10, the rotation of arms 30, 32 around rotation axis Γ. Adjustment system 28 comprises two setting means 68, 70, which enable modifying the position of pin joint 31 with respect to head 12 of bone 14 along two substantially perpendicular directions. According to the present embodiment, setting means 68, 70 are formed of settable screws manually actuated by a user.

The materials used to form the parts forming guiding device 10 are compatible with the sterility constraints specific to the medical field. The assembly of device 10 according to the first example of embodiment on head 12 of bone 14 is the following. A first assembly formed of seat 16, arm 30, and cutting guide 36, and a second assembly formed of seat 18 and of arm 32 are approximately arranged at the level of head 12 in substantially opposite fashion with respect to head 12. Seats 16, 18 are brought close together to insert end 40 of guide 36 into opening 42 of arm 32. Ball and socket joints 29, 34 compensate for the assembly clearances in the assembly of cutting guide 36 with arm 32. The position of arm 30 with respect to seat 16 is then accurately adjusted via adjustment system 28 to accurately define the position of rotation axis Γ. To simplify the kinematics of guiding device 10, the dimensions of arms 30, 32 are defined so that rotation axes Γ and Δ are parallel.

The operation of device 10 once attached to head 12 of bone 14 is the following. The actuation of motor 64 enables globally displacing cutting guide 36 with respect to head 12 of bone 14 around axis Γ. The actuation of motor 62 enables inclining cutting guide 36 around axis Δ, which determines the direction of driving shaft 48 of cutting tool 44 once the latter has been arranged at the level of cutting guide 36. The distance separating mill 46 and bearing surface 52 then enables selecting the position of the cutting plane from among a family of parallel cutting planes.

FIG. 3 schematically shows device 10 according to the present invention equipped with cutting tool 44 in the performing of two bone cuttings according to distinct cutting planes. In FIG. 3, the contour of head 12 of bone 14 is shown in stripe-dot lines in the absence of bone cuttings and in full lines once the cuttings have been performed. For a better visibility, arm 32 is shown in dotted lines. According to the example of implementation of bone cuttings illustrated in FIG. 3, the milling is performed frontally.

The axis of mill 46 is then arranged substantially perpendicularly to the cutting plane.

According to the example of bone cuttings illustrated in FIG. 4, the milling is performed laterally. The axis of mill 46 is then arranged substantially parallel to the cutting plane. As appears from FIGS. 3 and 4, the different bone cuttings are performed according to cutting planes which cut in straight lines parallel to a direction called the prosthesis axis. It is thus sufficient to provide a rotating motion around the prosthesis axis to position all the cutting planes. The device according to the present invention enables positioning cutting guide 36. To adjust the position of cutting guide 36, the present invention provides two adjustment mechanisms. The first adjustment mechanism is formed of adjustment system 28 with two degrees of freedom which enables positioning rotation axis F parallel to the prosthesis axis. The second adjustment mechanism is formed of two motors 62, 64 and enables, by the control of two degrees of freedom, positioning cutting guide 36. More specifically, the two motors 62, 64 rotate elements of device 10 according to two parallel rotation axes Γ, Δ. Rotation axis Γ is provided at the level of head 12. Rotation axis Δ rotates around rotation axis Γ. Such a device 10 with two degrees of freedom enables achieving all the desired configurations of head cutting planes as soon as rotation axis Γ is properly positioned.

Device 10 according to the present invention provides significant swinging angles of cutting guide 36 around rotation axis Γ. As an example, swingings greater than 100 degrees around rotation axis Γ may be reached, the inclination of cutting guide 36 around axis Δ being sufficient to reach all the desired cutting plane positions. The inclination of cutting guide 36 with respect to axis Δ especially enables selecting a lateral or front milling.

FIGS. 5 and 6 shows a second example of embodiment of guiding device 10 according to the present invention. Elements common with the first example of embodiment are indicated by identical reference numerals. According to the second example of embodiment of the present invention, seats 16, 18 are connected by a connection element 72 which goes around head 12 of bone 14 from one seat 16 to the other seat 18. As an example, connection element 72 has a "U", "V", "C", etc. shape. Adjustment system 28 is arranged between seat 16 and connection element 72. Seat 18 may be displaced, for example, by a screw mechanism, with respect to connection element 72 to be brought closer to or away from the other seat 16. Each seat 16, 18 comprises at least three picks 24.

A rigid body 76, attached to connection element 72, supports retro-reflecting faces 78 (six retro-reflecting faces being shown in FIGS. 5 and 6). Rigid body 76 belongs to a location system (not shown) capable of determining the position of connection element 72. The location system for example is of the type comprising a source emitting an infrared radiation and several sensors measuring the infrared radiation reflected by retro-reflecting faces 78. It should be noted that any system for locating connection element 72 may be used. As an example, the location system may be based on optical technology (like system POLARIS of NDI Company, Toronto, Canada), based on magnetic technology (like system Fastrack of Polhemus Inc, USA), or based on ultrasound technology (product of Zebris Company, Germany).

FIG. 6 shows the complete structure of cutting guide 10 according to the second example of embodiment of the present invention. Device 10 is intended to be used with a cutting tool (not shown) of oscillating saw type. Cutting guide 36 then comprises a planar slot 80 delimited by two upper and lower planar walls and in which the oscillating saw is inserted. According to the arrangement of cutting guide 36, the upper portion or the lower portion is confounded with the cutting plane. Like for the first embodiment, guide 36 is pivotally assembled around rotation axis A on arms 32, 30, themselves pivotally assembled on seats 16, 18 around rotation axis Γ. Motors 62, 64 are arranged on a base 82 mounted on arm 30. Motor 64 rotates arm 30 with respect to seat 16 around axis Γ and motor 62 rotates guide 36 with respect to arm 30 around axis Δ. It is advantageous to provide a fast and simple assembly of base 82 on arm 30. For this purpose, arm 30 may comprise at the level of a location or of several locations a surface with three grooves (not shown) distributed in a star and receiving balls arranged at the level of plate 82. Arm 30 further has a threading arranged at the center of the star-shaped groove distribution. The assembly of base 82 on the arm is then ensured by means of a screw maintaining block 82 against arm 30.

The assembly of device 10 according to the second example of embodiment of the present invention is performed by sufficiently spacing seats 16, 18 apart from each other to inert head 12 between the two seats 16, 18, approximately according to the desired final position. Seats 16, 18 are then brought closer to each other so that picks 24 of seats 16, 18 come in contact with head 12. Adjustment system 28 then enables accurately setting the relative position between connection element 72 and seat 16 to define the position of rotation axis Γ. The definitive fastening of seats 16, 18 to head 12 may be obtained by means of pins or fastening screws not shown. The adjustment of the position of rotation axis Γ by adjustment system 28 may be computer-assisted. Indeed, it may be provided to display on a display screen the theoretical position of rotation axis Γ provided from a modeling of bone 14 and the real position of rotation axis Γ obtained from the position of connection element 72 provided from rigid body 76.

The control to be applied to motors 62, 64 on positioning of device 10 to perform the bone cuttings may be provided by the computer based on the position of fastening element 72 provided from rigid body 76, from an initial position of cutting guide 36 obtained by temporarily applying a position tracking system at the level of slot 80 of cutting guide 36, and from operation parameters of motors 62, 64.

FIG. 7 illustrates in further detail an example of operation of adjustment system 28. Rotation axis Γ is defined by points A and D. As an example, in the first example of embodiment, point A corresponds to the center of ball and socket joint 34 and point D corresponds to the center of pin joint 31. Points B and C are on rotation axis Γ and respectively correspond to the center of setting means 70 and of setting means 68. An orthogonal reference frame in which axis (OZ) corresponds to the initial position of rotation axis Γ is defined.

From an initial position, setting means 70 enable displacing point B along direction (OX) in the positive or negative direction, and setting means 68 enable displacing point C along diction (OY) in the positive or negative direction. The adjustment of the position of rotation axis Γ is thus obtained by displacing points B and C which drive rotation axis Γ. A displacement of point B along direction (OX) by a given distance causes an inclination of rotation axis Γ around axis (OY) by an angle β and a displacement of point C along direction (OY) by a given distance causes an inclination of rotation axis Γ around axis (OX) by an angle α.

Each setting means 68, 70 may be formed of a carriage moving in a rail extending along direction (OX) or direction (OY), the carriage being actuated by a screw. It should be noted that, if the adjustment ranges are large enough for angle α and β to exceed 1°, it is preferable to enable points B and C to move along rotation axis Γ to adapt to the length change resulting from the linear displacement during adjustments. This can be obtained by using rails forming an arc of a circle.

FIG. 8 shows a third example of embodiment of the device according to the present invention. Elements common with the first example of embodiment are indicated by identical reference numerals. The third example of embodiment consists of only keeping a portion of the device according to the first example of embodiment. More specifically, the device according to the third example of embodiment is formed of seat 16, of adjustment system 28, of arm 30, and of guide 36. Rotation axes Γ and Δ are preferably maintained substantially parallel to each other and guide 36 preferably extends at least partly traversally to the bone head. As an example, guide 36 is shown in FIG. 8 with a length shorter than the length of the guide of FIG. 2. The operation of the device according to the third example of embodiment is similar to that of the device according to the first example of embodiment. The device according to the third example of embodiment is, for example, adapted to cuttings at the level of a single condyle of the knee.

According to a variation of the present invention, adjustment system 28 is controlled by electric motors. The accurate setting of the position of rotation axis Γ with respect to head 12 of bone 14 can then be computer-assisted.

The cutting guide according to the present invention has many advantages:

First, the device according to the present invention takes up a reduced volume, and thus does not require modifying conventional surgery techniques, especially as concerns the incisions to be performed to position the device.

Second, the cutting guide enables forming several distinct cutting planes at the level of the head of a bone by means of a single cutting guide.

Third, the cutting guide can easily be adapted to different cutting tools such as cutting mills or oscillating saws, simply by changing the cutting guide.

Fourth, electric motors can easily be assembled on the cutting device, enabling simple and accurate computer-assisted control of the device.

Of course, the present invention is likely to have various alterations and modifications which will occur to those skilled in the art. In particular, rigid body 76 may be temporarily fastened to connection element 72 by providing, for example, a slot at the level of connection element 72 in which a corresponding portion of a rigid body is temporarily inserted.

The invention claimed is:

1. A device for guiding a cutting tool capable of cutting bone portions at the level of the head of a femoral bone comprising:
    a seat configured for fastening to a side of said femoral bone adjacent to distal condyles where the femoral bone is to be cut, said seat being coupled to the femoral bone about a first rotation axis (Γ);
    means for adjusting in two substantially perpendicular directions the first rotation axis with respect to said seat including after the device is fastened to the femoral bone;
    an arm supporting first and second motors that are spaced a fixed distance from one another in all operating positions of the device, with one end of said arm being pivotally assembled on said seat according to the first rotation axis; and
    a cutting guide configured to guide the cutting tool and is pivotally assembled on the arm according to a second rotation axis (Δ), wherein the second motor is operatively coupled to the cutting guide for rotating the cutting guide about the second rotation axis, wherein a distance between the first and second rotational axes is also fixed in all operating positions of the device.

2. A device for guiding a cutting tool capable of cutting bone portions at the level of the head of a bone comprising:
    a seat configured to be fastened to a side of the bone at the level of said head, said seat being coupled to the bone about a first rotation axis (Γ);
    an adjustment system that is configured to adjust the position of the first rotation axis with respect to said seat;
    an arm having a first end pivotally coupled about said first rotation axis and an opposing second end;
    a guide configured for supporting the tool and pivotally coupled to the second end of the arm about a second rotation axis (Δ);
    a first motor supported by the arm and operatively coupled to the arm for rotating the arm about the first rotation axis; and
    a second motor supported by the arm and operatively coupled to the guide for rotating the guide about the second rotation axis, wherein the first and second motors move in tandem as the arm pivots and a distance between the first motor and the second motor is fixed in all operating positions of the device.

3. The device of claim 2, wherein the first and second motors are coupled to said device.

4. The device of claim 2, wherein the first and second motors are disposed along parallel axes.

5. The device of claim 2, wherein the first motor is axially aligned with the first rotation axis and the second motor is axially aligned with the second rotation axis.

6. The device of claim 2, wherein the adjustment system is disposed between the arm and the seat.

7. The device of claim 6, wherein the adjustment system is coupled to the seat with a ball and socket joint.

8. The device of claim 2, further comprising: a linkage coupled to the motor and the guide so as to translate rotation of the second motor into rotation of the guide.

9. The device of claim 2, wherein the guide includes a first groove with a first entrance in communication therein and a second groove with a second entrance in communication therein, the tool being insertable into one of the first and second grooves.

10. The device of claim 9, wherein the first and second grooves comprise longitudinal grooves spaced apart from one another and the tool includes a bearing surface that maintains a shaft of the tool in a direction substantially perpendicular to the second rotation axis when an operator applies the tool against the guide.

11. A device for guiding a cutting tool capable of cutting bone portions at the level of the head of a femoral bone comprising:
    a seat configured for fastening to a side of the femoral bone adjacent to distal condyles where the femoral bone is to be cut, said seat being coupled to the bone about a first rotation axis (Γ);
    an adjustment system that is configured to adjust the position of the first rotation axis with respect to said seat, wherein the adjustment system is constructed so that the first rotation axis can be adjusted in two substantially perpendicular directions with respect to the seat including after the device is fastened to the head of the bone;
    an arm having a first end pivotally coupled about said first rotation axis and an opposing second end, the arm being movable between multiple positions; and
    a guide configured for supporting the tool and pivotally coupled to the second end of the arm about a second rotation axis (Δ), wherein movement of the arm into one of the multiple positions results in the guide being positioned about the bone to allow for cutting of the bone portions at different locations while the seat remains fixed and wherein rotation of the guide about the second rotation axis permits the guide to be moved and positioned relative to the bone while the arm remains stationary;
    wherein a distance between the first rotation axis and the second rotation axis remains fixed in all operating positions of the device.

12. The device of claim 11, further comprising: a first motor operatively coupled to the arm for rotating the arm about the first rotation axis; and a second motor operatively coupled to the guide for rotating the guide about the second rotation axis.

13. The device of claim 12, wherein the first and second motors are supported by said arm such that the first and second motors move in tandem as the arm pivots and a distance between the first motor and the second motor is fixed in all operating positions of the device.

14. The device of claim 11, further comprising: a linkage coupled to the motor and the guide so as to translate rotation of the second motor into rotation of the guide.

15. The device of claim 11, wherein the guide includes a first groove with a first entrance in communication therein and a second groove with a second entrance in communication therein, the tool being insertable into one of the first and second grooves.

16. The device of claim 15, wherein the first and second grooves comprise longitudinal grooves spaced apart from one another and the tool includes a bearing surface that maintains a shaft of the tool in a direction substantially perpendicular to the second rotation axis when an operator applies the tool against the guide.

17. The guiding device of claim 1, wherein the seat of the device is fastened to the side of the bone with at least one pin.

18. The guiding device of claim 1, wherein the guide of the device includes a planar slot delimited by an upper and a lower planar wall in which the cutting tool is intended to be inserted into.

19. The guiding device of claim 18, wherein the cutting tool comprises an oscillating saw.

20. The guiding device of claim 1, wherein the cutting tool is a milling tool.

21. The guiding device of claim 1, in which the arm of the device is connected to the seat by an adjustment system, the adjustment system being arranged between said seat and said arm and being capable of modifying the position of said arm with respect to said seat such that the inclination of the first and second rotational axis is adjusted in the two substantially perpendicular directions.

22. The guiding device of claim 1, wherein a rigid body is attached to the device, the rigid body being locatable by a location system capable of determining the position the device in space.

23. The guiding device of claim 22 wherein the rigid body is comprised of at least three retro-reflecting markers capable of being sensed by infrared sensors by the location system.

24. The guiding device of claim 22, wherein the adjustment of the inclination of said rotational axis is performed under computer assisted control.

25. The guiding device of claim 24, wherein the theoretical and real positions of the rotational axis obtained by the rigid body and location system are displayed on a display screen.

26. The guiding device of claim 1, wherein the seat includes first and second seats spaced apart from one another and configured to be fastened to opposing sides of said bone with the bone being received in the space between the first and second seats, the first rotation axis ($\Gamma$) passing through the first and second seats.

* * * * *